United States Patent [19]

Kondratenko et al.

[11] 4,251,457

[45] Feb. 17, 1981

[54] PROCESS FOR PURIFICATION OF THE OFF-GASES RESULTING FROM THE PRODUCTION OF BENZOYL CHLORIDE FROM PHOSGENE

[76] Inventors: Vladimir I. Kondratenko, bulvar Verkhovnogo, Soveta, 10a, kv. 57; Ivan N. Novikov, ulitsa Malyshko, 19a, kv. 57; Isai N. Feldman, ulitsa Korneichuka, 38a, kv. 62, all of Kiev; Boris G. Moiseev, ulitsa Vatutina, 15, kv. 62, Dzerzhinsk Gorkovskoi oblasti; Valery Y. Kolesnikov, ulitsa Sverdlova, 84a, kv. 52, Dzerzhinsk Gorkovskoi oblasti; Valentin I. Nefedov, ulitsa Popova, 14, kv. 8, Dzerzhinsk Gorkovskoi oblasti; Jury A. Fudaler, ulitsa Griboedova, 27, kv. 34, Dzerzhinsk Gorkovskoi oblasti, all of U.S.S.R.

[21] Appl. No.: 47,250

[22] Filed: Jun. 11, 1979

[30] Foreign Application Priority Data

Jul. 24, 1978 [SU] U.S.S.R. .............................. 2649052

[51] Int. Cl.³ ............................................. C07C 63/10
[52] U.S. Cl. ................................................. 260/544 K
[58] Field of Search ................................... 260/544 K

[56] References Cited

U.S. PATENT DOCUMENTS

2,764,607  9/1956  Hieserman ...................... 260/544 K

FOREIGN PATENT DOCUMENTS

4322779  6/1966  Japan ................................. 260/544 K
737442  9/1955  United Kingdom ................ 260/544 K

*Primary Examiner*—Paul J. Killos
*Attorney, Agent, or Firm*—Fleit & Jacobson

[57] ABSTRACT

A process for purification of the off-gases resulting from the production of benzoyl chloride by phosgenation of benzoic acid from phosgene comprising recovery of phosgene from said off-gases by means of a selective absorbent, i.e. benzoyl chloride at a temperature within the range of from 1° to 40° C. The recovered phosgene is recycled to the production of benzoyl chloride. The process is technologically simple, it makes possible to purify the off-gases without decomposition of phosgene thus preventing pollution of the environments; it also makes possible to simplify utilization of hydrogen chloride contained in the off-gases and, thereby, simplify preparation of commercial hydrochloric acid.

2 Claims, No Drawings

PROCESS FOR PURIFICATION OF THE OFF-GASES RESULTING FROM THE PRODUCTION OF BENZOYL CHLORIDE FROM PHOSGENE

FIELD OF THE INVENTION

The present invention relates to purification of the off-gases and, more specifically, to processes of the purification of the off-gases resulting from the production of benzoyl chloride produced by phosgenation of benzoic acid from phosgene. In said off-gases, in addition to the unreacted phosgene, there are contained hydrogen chloride, carbon dioxide and traces of benzoyl chloride.

BACKGROUND OF THE INVENTION

Known in the art is a commercial process for purification of the off-gases resulting from the production of benzoyl chloride prepared by phosgenation of benzoic acid from phosgene. This process comprises passing the off-gases successively through two packed columns, whereinto water is fed counter-currently to the off-gases at a temperature of from 70° to 85° C. while into the other column an aqueous ammonia solution is fed at the same temperature. The content of phosgene in gases after said purification does not exceed 0.5 mg/m$^3$.

This prior art process has a disadvantage residing in decomposition of phosgene which excludes recycling thereof to the production of benzoyl chloride. Besides, utilization of hydrogen chloride from the resulting diluted aqueous solution is complicated, which hinders the production of commercial hydrochloric acid and increases the amount of waste waters.

Also known are processes for purification of the off-gases resulting from other kinds of manufacture from phosgene, e.g. from the production of chloroformates or alkylchlorides with the use of phosgene such as hydrogenation (cf. USSR Inventor's Certificate No. 181621, Cl. B 01 d 53/04), passing the off-gases through a bed of activated alumina at a temperature within the range of from 110° to 200° C. (cf. U.S. Pat. No. 3,789,580 Cl. B 01 d 53/04) or through a bed of aluminium at a temperature within the range of from 300° to 600° C. (cf. FRG Pat. No. 2,115,859 Cl. C 01 d 7/58), washing of the off-gases with an alkali solution with the addition of minor amounts of ammonia (cf. FRG Pat. No. 2,531,545 Cl. B 01 d 53/02), treatment of the off-gases with ethanol at a temperature within the range of from 0° to 100° C. under atmospheric or elevated atmospheric pressure (cf. U.S. Pat. No. 3,142,535 Cl. 23–154).

The above-described purification processes exclude recycling to the production process, e.g. of chloroformates or alkylchlorides, since decomposition of phosgene occurs as a result of purification.

Also known in the art is a process for purification of the off-gases resulting from the production of isocyanates from phosgene, wherein the off-gases containing phosgene and hydrogen chloride are cooled to a temperature below the boiling temperature of phosgene (+8.2° C.) but above the boiling point of hydrogen chloride (−85.1° C.) and passed counter-currently through a bed of liquid phosgene (cf. French Pat. No. 1,089,476 Cl. C 07 C).

The use of liquid phosgene as an absorbent for recovery of phosgene from the off-gases has certain disadvantages:

1. Phosgene has a high vapour tension even at low temperatures. For this reason, prior to absorption of phosgene it is necessary to preliminary cool the off-gases. Despite the cooling, during absorption a substantial entrainment of the absorbent per se and the up-gas phosgene is possible along with inert gases. In addition, at a temperature below 0° C. clogging of pipelines is possible along with elevation of pressure in the system due to congelation of benzoyl chloride. All this results in a complicated technology of purification of the off-gases.

2. Due to a high toxicity of phosgene, special safety measures are required. The use of phosgene as an absorbent impairs labour conditions and results in pollution of the environments.

SUMMARY OF THE INVENTION

It is an object of the present invention to provide a process for purification of the off-gases resulting from the production of benzoyl peroxide prepared by phosgenation of benzoic acid from phosgene which would be technologically simple.

It is another object of the present invention to provide a process which would make it possible to purify the off-gases without decomposition of phosgene.

Still another object of the present invention is to provide such a process for purification of the off-gases resulting from the production of benzoyl chloride from phosgene which would prevent pollution of the environments.

It is also an object of the present invention to provide such purification process which would make it possible to simplify utilization of hydrogen chloride contained in the off-gases and, thereby, simplify the manufacture of commercial hydrochloric acid.

These and other objects of the present invention are accomplished by a process for purification of the off-gases resulting from the production of benzoyl chloride prepared by phosgenation of benzoic acid from phosgene, wherein phosgene is recovered from said off-gases by means of a selective absorbent, i.e. benzoyl chloride, at a temperature within the range of from 1° to 40° C., preferably at 1° to 20° C., whereafter the recovered phosgene is recycled to the process of production of benzoyl chloride.

The use of benzoyl chloride as an absorbent has the following advantages:

1. Selectivity of recovery of phosgene from the off-gases (benzoyl chloride does not practically dissolve hydrogen chloride and carbon dioxide and well dissolves phosgene).

2. A high degree of purification of the off-gases from phosgene. Thus, the content of phosgene in the off-gases is reduced after absorption conducted at the temperature of 20° C. from 3.92 to 0.24% by volume, i.e. by more than 16 times.

3. A low volatility of benzoyl chloride within the range of temperatures employed.

4. The recovered phosgene is readily recycled to the process for the production of benzoyl chloride.

5. An insufficient residual content of phosgene in the off-gases after absorption of benzoyl chloride results in lowered consumption of water required for decomposition of the residual amount of the non-recovered phosgene. This, in turn, simplifies utilization of hydrogen chloride from the off-gases and, thereby, simplify the manufacture of hydrochloric acid.

Recovery of phosgene from the off-gases resulting from the production of benzoyl chloride according to the process of the present invention is conducted at a temperature within the range of from 1° to 40° C. This temperature range is limited, on the one hand, by the congelation temperature of the absorbent per se (0.5° C.) and, on the other hand, by lowered solubility of phosgene in benzoyl chloride and possibility of entrainment of the absorbent at temperatures of above 40° C.

DETAILED DESCRIPTION OF THE INVENTION

The process for purification of the off-gases resulting from the production of benzoyl chloride prepared by phosgenation of benzoic acid from phosgene is effected in the following preferable manner.

The off-gases resulting from the production of benzoyl chloride containing the unreacted phosgene, hydrogen chloride, carbon dioxide and traces of benzoyl chloride are preliminary cooled to the temperature at which phosgene is to be recovered i.e. to a temperature within the range of from 1° to 40° C. Then the off-gases are fed from the bottom into an absorber provided with a cooling jacket and packing and plates. Into the same absorber counter-currently benzoyl chloride is fed from the top at a temperature within the range of from 1° to 40° C. In the absorber phosgene is dissolved in benzoyl chloride. Phosgene dissolved in benzoyl chloride is recycled to the production of benzoyl chloride. Furthermore, it is possible to recycle phosgene to the process with a preliminary recovery thereof from the solution of benzoyl chloride by purging with nitrogen or rectification.

The gases from the absorber containing 1 vol.% of the non-recovered phosgene, hydrogen chloride and carbons dioxide with traces of benzoyl chloride are passed through the system consisting of several columns with packing, sprayed with hydrochloric acid at a temperature within the range of from 70° to 100° C. to give, as a result, decompostion of the unrecovered phosgene to hydrogen chloride and carbon dioxide and, consequently, production of commercial hydrochloric acid. Therefore, utilization of hydrogen chloride with the formation of commercial hydrochloric acid is effected by means of a technologically simple efficient method using a typical scheme of a sanitary post-purification of gases. It is advisable to perform this sanitary post-purification of gases so as to complete it by treatment of the gases with an aqueous-ammonia solution.

For a better understanding of the present invention some specific Examples are given hereinbelow by way of illustration.

EXAMPLE 1

Recovery of phosgene from the off-gases resulting from the production of benzoyl chloride prepared by phosgenation of benzoic acid is effected by absorption of phosgene with benzoyl chloride at a temperature of from 1° to 4° C. The process is effected in an absorber comprising a cylindrical bubbling-type apparatus with the height of 200 mm, diameter 27 mm, provided with a water jacket and Schott filter. The height of the working layer of the absorbent (benzoyl chloride) is 150 mm.

Through the absorber with benzoyl chloride the off-gases are passed at a temperature of 1°-4° C. at the rate of 1, 3 l/hr for 4 hours; the off-gases has the following composition, percent by volume: $COCl_2$ 3.92; $C_6H_5COCl$ 0.25; $CO_2$ 47.84; $HCl$ 47.74; $N_2$ 0.19; $O_2$ 0.05.

The content of phosgene in the gases effluent from the absorber is determined by the titrometric method based on liberation of iodine from a solution of sodium iodide in acetone and titration of the evolved iodine with a solution of sodium thiosulphate. The content of phosgene in the gases after the absorber is 0.24% by volume.

Phosgene dissolved in benzoyl chloride is recycled to the production of benzoyl chloride.

The gases after the absorber are fed to the sanitary post-purification to decompose the residual amounts of phosgene and recovery of hydrogen chloride using hydrochloric acid and an aqueo-ammonium solution.

EXAMPLE 2

Recovery of phosgene from the off-gases is performed following the procedure of Example 1 hereinbefore. The difference resides in the composition of the off-gases which is the following, percent by volume: $COCl_2$ 40, $C_6H_5COCl$ 0.05, $CO_2$ 42.65; $HCl$ 17.3.

The content of phosgene in the gases after the absorber is equal to 0.35% by volume.

Phosgene, after purging with nitrogen from the solution of benzoyl chloride, is recycled to the production of benzoyl chloride.

EXAMPLE 3

Recovery of phosgene from the off-gases resulting from the production of benzoyl chloride is effected by absorption of phosgene with benzoyl chloride at the temperature of 6° C. The process is conducted in a cylindrical absorber with the height of 400 mm, diameter of 27 mm provided with a water-jacket and filled with glass packing with the diameter of 3 mm to the height of 350 mm. The off-gases have the composition similar to that of Example 2. The off-gases are passed upwardly from the bottom portion of the absorber at a rate of 0.4 to 0.6 m/sec. From the top of the absorber, benzoyl chloride is fed at the temperature of 6° C. at the spraying density of 2–2.5 ml/cm$^2$.min.

The content of phosgene in the gases after the absorber is 0.2 vol.%.

Phosgene, after separation thereof by rectification from the solution of benzoyl chloride is recycled to the production of benzoyl chloride.

EXAMPLE 4

Recovery of phosgene from the off-gases resulting from the production of benzoyl chloride is effected by absorption of phosgene with benzoyl chloride at the temperature of 40° C. The off-gases have the following composition, percent by volume: $COCl_2$ 3.92; $C_6H_5COCl$ 0.25; $CO_2$ 47.84; $HCl$ 47.75; $N_2$ 0.19; $O_2$ 0.05.

The process is conducted in the absorber described in the foregoing Example 3 at the same supply rate of the off-gases and the same spraying rate and density.

The content of phosgene in the gases after the absorber is equal to 0.8 vol.%.

Phosgene dissolved in benzoyl chloride is recycled to the production of benzoyl chloride.

What is claimed is:

1. A process for purification of the offgases resulting from the production of benzoyl chloride by phosgenation of benzoic acid by phosgene comprising the steps of selectively absorbing phosgene in the off-gases with benzoyl chloride at a temperature from 1° to 40° C. and recycling the recovered phosgene to the production of benzoyl chloride.

2. The process of claim 1, wherein the temperature is from 1° to 20° C.

* * * * *